United States Patent
Olive et al.

(10) Patent No.: US 10,005,839 B2
(45) Date of Patent: *Jun. 26, 2018

(54) ANTAGONIST OF THE BTLA/HVEM INTERACTION FOR USE IN THERAPY

(71) Applicants: INSERM (Institut National de la Sante et de la Recherche Medicale), Paris (FR); Institut Jean Paoli & Irene Calmettes, Marseilles (FR); Universite d'Aix Marseille, Marseilles (FR); Centre National de la Recherche Scientifique—CNRS, Paris (FR)

(72) Inventors: Daniel Olive, Marseilles (FR); Christine Pasero, Marseilles (FR); Julie Gertner-Dardenne, Valbonne-Sophia Antipolis (FR)

(73) Assignees: INSERM (INSTITUT NATIONAL DE LA SANTE ET DE LA RECHERCHE MEDICALE), Paris (FR); INSTITUT JEAN PAOLI & IRENE CALMETTES, Marseille (FR); UNIVERSITE D'AIX-MARSEILLE, Marseille (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/891,501

(22) PCT Filed: Feb. 21, 2014

(86) PCT No.: PCT/EP2014/053422
§ 371 (c)(1),
(2) Date: Nov. 16, 2015

(87) PCT Pub. No.: WO2014/183885
PCT Pub. Date: Nov. 20, 2014

(65) Prior Publication Data
US 2016/0090420 A1    Mar. 31, 2016

(30) Foreign Application Priority Data
May 17, 2013    (EP) .................................... 13305639

(51) Int. Cl.
*C07K 16/28* (2006.01)
*A61K 39/00* (2006.01)

(52) U.S. Cl.
CPC ...... *C07K 16/2866* (2013.01); *C07K 16/2818* (2013.01); *C07K 16/2875* (2013.01); *A61K 39/00* (2013.01); *C07K 2317/51* (2013.01); *C07K 2317/515* (2013.01); *C07K 2317/55* (2013.01); *C07K 2317/74* (2013.01); *C07K 2317/76* (2013.01)

(58) Field of Classification Search
CPC ...................................................... C07K 16/28
USPC ................... 530/388.1, 387.3; 435/326, 325; 424/133.1
See application file for complete search history.

(56) References Cited

U.S. PATENT DOCUMENTS

| 8,318,166 B2 * | 11/2012 | Olive ............... A61K 39/39558 424/141.1 |
| 2010/0196386 A1 * | 8/2010 | Olive ............... A61K 39/39558 424/141.1 |

FOREIGN PATENT DOCUMENTS

| WO | 2007/001459 | 1/2007 |
| WO | 2010/106051 | 9/2010 |

OTHER PUBLICATIONS

International Search Report in PCT/EP2014/053422 dated Mar. 14, 2014.
Pasero et al., "Interfering with coinhibitory molecules: BTLA/HVEM as new targets to enhance anti-tumor immunity," Immunol. Lett., 151(1-2):71-75 (2013) XP002713688.
M'Hidi Hasni et al., "Hight Expression of the Inhibitory Receptor BTLA in T-Follicular Helper Cells and in B-Cell Small Lymphocytic Lymphoma/Chronic Lymphocytic Leukemia," Am J. Clin Pathol., 132(4):589-596 (2009) XP009135450.
Olive, "Lymphocyte coreceptors," M/S Medecine Sciences, Societe des Periodiques Flammarion, Paris, FR, 22(12):1069-1074 (2006) XP009135449.

* cited by examiner

*Primary Examiner* — Yan Xiao
(74) *Attorney, Agent, or Firm* — Whitham, Curtis & Cook, P.C.

(57) ABSTRACT

Antagonist of the BTLA/HVEM interaction for use in therapy The present invention relates to an antagonist of the BTLA/HVEM interaction for use in therapy, wherein said antagonist increases the proliferation of Vγ9Vδ2 T cells.

4 Claims, 4 Drawing Sheets

ANTAGONIST OF THE BTLA/HVEM INTERACTION FOR USE IN THERAPY

The present application is filed pursuant to 35 U.S.C. 371 as a U.S. National Phase application of International Patent Application No. PCT/EP2014/053422, which was filed Feb. 21, 2014, claiming the benefit of priority to European Patent Application No. 13305639.0, which was filed on May 17, 2013. The entire text of the aforementioned applications is incorporated herein by reference in its entirety.

FIELD OF THE INVENTION

The present invention relates to an antagonist of the BTLA/HVEM interaction for use in therapy.

BACKGROUND OF THE INVENTION

Vγ9Vδ2 cells represent a major peripheral blood T cell subset in humans displaying a broad reactivity against microbial agents and tumors. They have the ability to simultaneously recognize and respond to phosphorylated non-peptide antigens (phosphoantigens, PAg), molecules found on a wide variety of pathogenic organisms and tumor cells in a HLA unrestricted fashion. Accordingly, Vγ9Vδ2 T cells are involved in tumor immune surveillance notably against carcinomas and hematologic malignancies.

Maintenance of lymphocyte population size is usually achieved by balancing the generation of new cells and clonal expansion with cell death. However, the homeostasis of Vγ9Vδ2T cells remain poorly understood. The size of the Vγ9Vδ2T cell pool is regulated by the availability of IL-15 and IL-7, and their homeostasis is maintained in competition with αβ T cells and NK cells. When both αβ and γδ cell types are adoptively transferred in equal numbers into TCRβ$^{-/-}$δ$^{-/-}$ mice, αβ T cells rapidly outgrow γδ T cells.

Thus, γδ T cells have a substantial disadvantage compared to αβ T cells during their expansion. Molecular pathways regulating the proliferation and homeostasis of γδ T cells are still not known. By comparison, it is well accepted that co-receptors positively or negatively regulate αβT cell activation, expansion and survival.

Among these co-receptors, molecules of the CD28:B7 family have a potent regulatory effect on TCR-mediated activation. Some of these co-receptors like PD-1 are also able to modulate Vγ9Vδ2 T cells proliferation.

BTLA, a recently described member of the CD28:B7 family structurally related to CTLA-4 and PD-1 is expressed by most lymphocytes. Its ligand, herpes virus entry mediator (HVEM), is a member of the TNF receptor superfamily expressed by T, B, and NK cells, dendritic cells and myeloid cells. BTLA-deficient mice exhibit a normal B and T cells development. However, mature lymphocytes from these mice, display higher frequencies of memory T cells and generate more memory-like responses. 20 Moreover, BTLA-deficient mice and in vitro observations obtained using agonist anti-BTLA antibodies and HVEM-Ig fusion proteins have evidenced BTLA as a negative modulator of immune responses against self- and allo-antigens and antigen independent homeostatic expansion of CD4+ and CD8+ T cells.

Indeed dysfunction of the BTLA-HVEM pathway is suspected to play a role in the pathogenesis of various auto-immune and neoplastic diseases, especially in the dysfunction of innate immunity in inflammatory diseases. Only few functional data about BTLA are available in Humans.

Cross-linking of BTLA with an agonistic mAb can inhibit αβ T cell proliferation and the production of IFN-γ and IL-10 in response to anti-CD3 stimulation.

Moreover, BTLA stimulation inhibits the function of both human melanoma-specific and CMV-specific T cells.

Among haematological malignancies, the inventors have previously shown that BTLA is expressed by neoplastic cells in B-CLL, but not in most B-non-Hodgkin's lymphomas (NHL), although various reactive immune cells of the lymphoma microenvironment are BTLA-positive.

The BTLA ligand, HVEM, displays frequent abnormalities in human B cell malignancies, especially in follicular lymphoma (FL), which harbor a high frequency of mutations in the TNFRSF14 (HVEM) gene. These mutations typically lead to the truncation of TNFRSF14 and are accompanied by the deletion of the wild type allele, which suggests a possible role for HVEM as a tumor suppressor gene.

The inventors have shown that BTLA expression is regulated not only during Vγ9Vδ2 T cell differentiation but also upon TCR-mediated activation. BTLA blockade improves TCR signaling. Furthermore, the inventors demonstrated that its interaction with HVEM negatively regulates TCR-independent and TCR-dependent Vγ9Vδ2 T cell proliferation, and that HVEM positive FL cells efficiently inhibited Vγ9Vδ2 T cell proliferation.

SUMMARY OF THE INVENTION

The inventors have shown for the first time that BTLA is implicated in the regulation of Vγ9Vδ2 T cells proliferation and differentiation and that the BTLA-HVEM pathway is a major actor in the control of Vγ9Vδ2 T cells proliferation. Therefore, the inventors have developed a new highly promising strategy for use in therapy.

A first object of the invention thus relates to an antagonist of the BTLA/HVEM interaction for use in therapy, wherein said antagonist increases the proliferation of Vγ9Vδ2 T cells.

Preferably, said antagonist is used in a method of treatment of haematological malignancies, solid tumors, auto-immune diseases or infections.

In one embodiment, said antagonist is chosen from antibodies directed against HVEM and fragments thereof which block the interaction between BTLA and HVEM. Preferably, said antagonist of the BTLA/HVEM interaction is a monoclonal antibody obtainable from the hybridoma deposited at the Collection Nationale de Cultures de Microorganismes on May 16, 2013, under the number CNCM I-4752.

In another embodiment, said antagonist is chosen from antibodies directed against BTLA and fragments thereof which block the interaction between BTLA and HVEM.

Typically, said antibody is chosen among polyclonal antibody, monoclonal antibody, chimeric antibody, humanized antibody, or an antibody fragments.

Said fragment of the antibody which blocks the interaction between BTLA and HVEM interaction is chosen Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments.

A second object of the invention relates to a hybridoma cell line suitable for obtaining anti-HVEM monoclonal antibodies which block the interaction between HVEM and BTLA and increase the proliferation of Vγ9Vδ2 T cells.

DETAILED DESCRIPTION OF THE INVENTION

A first object of the invention relates to an antagonist of the BTLA/HVEM interaction for use in therapy, wherein said antagonist increases the proliferation of Vγ9Vδ2 T cells.

Vγ9Vδ2 cells, the major γδ T cell subset in human peripheral blood, represent a T-cell subset displaying reactivity against microbial agents and tumors. The biology of Vγ9Vδ2T cells remain poorly understood. The inventors have shown that the interaction between B and T Lymphocyte Attenuator (BTLA) and Herpes Virus Entry Mediator (HVEM) is a major regulator of Vγ9Vδ2 T cell proliferation control. BTLA was strongly expressed at the surface of resting Vγ9Vδ2T cells and inversely correlated with T cell differentiation.

The inventors observed a close physical membrane localization of TCR and BTLA after TCR signaling. BTLA-HVEM blockade by mAbs resulted in the enhancement of Vγ9Vδ2 TCR mediated signaling, whereas BTLA-HVEM interaction led to a decrease in phosphoantigen mediated proliferation by inducing a partial S phase arrest.

These data also indicate that BTLA-HVEM might participate in the control of γδ T cells differentiation. In addition, the proliferation of autologous γδ T cells after exposition to lymphoma cells was dramatically reduced through BTLA-HVEM interaction. These data indicate that HVEM dysregulation may play a role in lymphomagenesis by interacting with Vγ9Vδ2 cell proliferation.

The invention thus relates to an antagonist of the BTLA/HVEM interaction for use in therapy, wherein said antagonist increases the proliferation of Vγ9Vδ2 T cells.

The term "HVEM", as used herein, is intended to encompass all synonyms including, but not limited to, "Herpes Virus Entry Mediator", "HVEA", "Herpes Virus Entry Mediator A", "TNFRSF14", "Tumor Necrosis Factor Receptor Superfamily Member 14", "TNR14", "LIGHTR", "LIGHT receptor", "TR2", "TNF Receptor-like", "ATAR", "Another TRAF-Associated Receptor". TNFRSF14 is the HUGO (Human Genome Organization) Gene Nomenclature Committee (HGNC) approved symbol. The UniProtKB/Swiss-Prot "Primary Accession Number" for HVEM is Q92956. The "Secondary Accession Numbers" are Q8WXR1, Q96J31 and Q9UM65.

The term BTLA refers to a ligand of HVEM. By "ligand" is meant a compound which binds to a receptor molecule to form a receptor-ligand complex. So far, several ligands have been identified which bind to HVEM.

Two of these ligands, LIGHT and LTα, are member of the TNF family of molecules (Morel, Y. et al., 2000; Mauri, D. N. et al., 1998 and Harrop, J. A. et al., 1998). Structurally, members of the TNF family are generally expressed as single-pass type 2 transmembrane, homotrimer or heterotrimer, glycoproteins. Following their expression as transmembrane proteins, they are cleaved by proteolytic action to produce a soluble form of the ligand.

The third ligand for HVEM, BTLA, a type 1 transmembrane glycoprotein, is a member of the immunoglobulin (Ig) superfamily of molecules and is closely related to CD28 (Gonzalez, L. C. et al., 2005).

The fourth ligand, glycoprotein D (gD), is a structural component of the herpes simplex virus (HSV) envelope, and is essential for HSV entry into host cells (Montgomery, R. I. et al., 1996; Hsu, H. et al., 1997; Kwon, B. S. et al., 1997; Tan, K. B. et al., 1997; Marsters, S. A. et al., 1997; Wallach, D. et al., 1999; Collette, Y. et al., 2003; Harrop, J. A. et al., 1998; Gonzalez, L. C. et al., 2005 and Whitbeck, J. C. et al., 1997).

Recently, CD160 was shown to be a newly identified ligand for HVEM.

Binding studies (Gonzalez, L. C. et al., 2005 and Sedy, J. R. et al., 2005) which were later supported by crystallography (Compaan, D. M. et al., 2005) indicate that BTLA interacts with the most membrane-distal CRD region of HVEM. The membrane-distal CRD1 region of HVEM has also been implicated in the interactions with HSV-gD, with additional contributions from CRD2 (Compaan, D. M. et al., 2005 and Carfi, A. et al., 2001). Despite the sequence and structural dissimilarities between BTLA and HSV-gD, the crystal structure studies also show that their binding sites on HVEM cover largely overlapping surfaces (Compaan, D. M. et al., 2005 and Carfi, A. et al., 2001).

In one embodiment, said antagonist is used in a method of treatment of a treatment of a haematological malignancy. Hematologic malignancies include but are not limited to lymphoid cell neoplasms such as chronic lymphocytic leukaemia (CLL), non-Hodgkin lymphoma (NHL), small lymphocytic lymphoma (SLL), and mantle cell lymphoma (MCL). More specifically, non-Hodgkin lymphoma (NHL) include B and T non-Hodgkin lymphoma. Furthermore, cell lymphoid neoplasms include B, NK and T cell lymphoid neoplasms.

Preferably, said haematological malignancy is a lymphoma.

Indeed, the inventors have put in light that BTLA stimulation of Vγ9Vδ2T cell is a highly promising mechanism of immune escape by lymphoma cells.

More preferably, said lymphoma is selected among Non-Hodgkin lymphomas and Hodgkin lymphomas.

As used herein, the term "leukemia" has generally been used to define hematologic malignancies of the blood or bone marrow characterized by abnormal proliferation of leukocytes. The principal subtypes of leukemia are identified on the basis of malignancy involving lymphoid (e.g. T or B lymphocytic lineage) or myeloid (e.g. granulocytic, erythroid or megakaryocytic lineage) cells, and whether the disease is acute or chronic in onset [Freireich, E. J. et al., 1991].

As used herein, the term "lymphoma" covers a heterogeneous group of neoplasms of lymphoid tissue. Lymphomas are broadly categorized under Hodgkin lymphoma, and T-cell (T-NHL) and B-cell (B-NHL) non-Hodgkin lymphomas. A World Health Organization (WHO) classification has recently been published (discussed later in this application), and diagnostic guidelines have been established based on this classification [Jaffe, E. S. et al., 2004].

Chronic Lymphocytic Leukemia (CLL) is a form of lymphocytic leukemia characterized by slow but progressive accumulation of lymphocytes in the bone marrow and blood. Depending on the stage of the disease, lymph node and spleen enlargement occur commonly. Although CLL may be of T cell or B cell origin, over 85% of the cases are of B-cell origin. Current understanding suggests that CLL is a heterogeneous disease originating from B lymphocytes that differ in their activation and maturation states and cellular subgroup (see [Kuppers, R., 2005]). The disease may result both from decreased apoptosis as well as increased proliferation of the leukemic B cells. CLL cells are usually clonal in origin, and express the following cell surface markers:

CD19, CD20, CD21, and CD24. In addition, they express CD5 which is more typically found on T cells (see [Chiorazzi, N, and al., 2005]).

CLL is considered a subgroup of "non-Hodgkin's lymphoma" (NHL) and together with the closely related disease "small lymphocytic lymphoma" (SLL) which presents primarily in the lymph nodes, corresponds to around 20% of all NHL cases. CLL is the most common leukemia in adults in the US and most of Western Europe. The National Cancer Institute (NCI) estimate for the incidence of CLL is about 10.000 new cases in the US per year. Clinical manifestations of CLL occur predominantly after the age of 55. The incidence rate for men is higher than for women, with men almost twice as likely to acquire the disease as women.

CLL represents an unmet medical need as there are limited options for treatment.

The most common treatments for NHL are chemotherapy, in particular a combination regimen called CHOP (for Cytoxan, Hydroxyrubicin [Adriamycin], Oncovin [Vincristine], Prednisone), and radiation therapy. In some cases, surgery and bone marrow transplantation have also been used. More recently, there has been an increase in the use of biopharmaceutical agents, especially monoclonal antibodies, such as rituximab and alemtuzumab. Other combination approaches include the use of biopharmaceuticals such as rituximab with chemotherapy. Although these treatments have significantly improved the management of B-lymphoid malignancies, among their deficiencies include non-responsiveness of many patients to these regimens (some patients become refractory to some or all these approaches), and the side effects and complications which result from the use of these treatments. Among the most common side effects of chemotherapy are nausea and vomiting (which is generally managed with the use of antiemetics), alopecia (which is generally reversed over time after completion of treatment), and leukopenia, especially neutropenia. Neutropenia generally develops in the second week. During this period, many clinicians recommend prophylactic use of ciprofloxacin. If a fever develops in the neutropenic period, urgent medical assessment is required for neutropenic sepsis, as infections in patients with low neutrophil counts may progress rapidly. With respect to rituximab, first infusion reaction, lymphopenia, infectious complications such as viral reactivation including Hepatitis B and Progressive Multifocal Leukoencephalopathy (PML), mucocutaneous reactions, and renal complications have been reported. In the case of alemtuzumab, serious hematologic toxicities can occur, including pancytopenia, bone marrow hypoplasia, autoimmune idiopathic thrombocytopenia, and autoimmune hemolytic anemia. In some cases, these toxicities can accelerate morbidity and mortality rates.

In another embodiment, said antagonist of the BTLA/HVEM interaction is used in a method of treatment of a solid tumor.

As used herein, the term "solid tumor" refers to an abnormal mass or population of cells that result from excessive cell division, whether malignant or benign, and all pre-cancerous and cancerous cells and tissues.

Examples of solid tumors include prostate cancer, pancreatic cancer, breast cancer, brain cancer, bladder cancer, prostate cancer, colon cancer, intestinal cancer, lung cancer, stomach cancer, cervical cancer, ovarian cancer, liver cancer, skin cancer, colorectal cancer, endometrial carcinoma, salivary gland carcinoma, kidney cancer, thyroid cancer, various types of head and neck cancer.

Preferably, said solid tumor is selected among prostate and pancreatic cancer.

In another embodiment, said antagonist of the BTLA/HVEM interaction is used in a method of treatment of an autoimmune disease.

The immune system has control mechanisms which prevent it from attacking self tissue. When these mechanisms do not function properly or when they break down, they can result in the development of autoimmunity or autoimmune diseases. Autoimmunity represents a broad spectrum of diseases from the organ specific to the non-organ specific. At one end of the spectrum, Hashimoto's thyroditis typifies the highly organ specific diseases where the destructive lesion is directed at one organ only. At the other end of the spectrum, lupus erythematosus (SLE) represents the non-organ specific diseases where the tissues involved are widespread throughout the body. With improvements of immunobiology, and advances in molecular and diagnostic tools, it is becoming progressively evident that most organ or tissue systems can be subject to the autodestructive potential of autoimmune diseases as is shown in the following list. Thus among the autoimmune diseases are included: Addison's disease, ankylosing spondylitis, aplastic anemia, autoimmune hemolytic anemia, autoimmune hepatitis, coeliac disease, Crohn's disease, dermatomyositis, Goodpasture's syndrome, Graves' disease, Guillain-Barré syndrome, Hashimoto's disease, idiopathic leucopenia, idiopathic thrombocytopenic purpura, insulin dependent diabetes mellitus (Type 1 diabetes), male infertility, mixed connective tissue disease, multiple sclerosis (MS), myasthenia gravis, pemphigoid, pemphigus vulgaris, pernicious anemia, phacogenic uveitis, primary biliary cirrhosis, primary myxoedema, Reiter's syndrome, rheumatoid arthritis (RA), scleroderma, Sjögren's syndrome, stiff man syndrome, systemic lupus erythematosus (SLE), thyrotoxicosis, ulceritive colitis, and Wegener's granulomatosis.

The etiology of autoimmune diseases is not completely understood. In some instances, mechanisms of molecular mimicry have been proposed whereby a productive anti-bacterial or anti-viral response may inadvertently result in the development of immunological responses to self tissue. In addition, inherited or genetic predispositions are known to contribute to the development of many of these diseases.

Both lymphoid and myeloid lineage cells have been implicated in the development of autoimmune diseases. Autoreactive T and B lymphocytes determine the principal clinico-pathologic features of each disease and the tissue involved. T lymphocytes may attack self tissue directly whereas B cells secrete autoreactive antibodies. In SLE, copious of self reactive antibodies including antibodies to double-stranded DNA are produced which are believed to cause or exacerbate kidney damage. Myeloid lineage cells such are macrophages help to maintain, amplify and extend the immune attack against self tissue by providing cytokine and chemokine responses such as TNF-α, and IL-8, as well as by serving as effector cells for the autodestructive processes. A role for TNF-α, has been clearly established for RA and Crohn's disease which are now known to respond to anti-TNF-α therapies. In the case of RA, myeloid lineage cells are believed to differentiate to osteoclasts thus causing bone damage and destruction of synovial linings with the inflamed joints. RA patients have also been shown to respond to treatments directed against B cells, such as anti-CD20 antibody therapy.

In still another embodiment, said antagonist of the BTLA/HVEM interaction is used in a method of treatment of an infection.

Examples of infections include, but are not limited to, viral, bacterial, parasitic or fungal infections such as chronic hepatitis, lung infections, lower respiratory tract infections, bronchitis, influenza, pneumoniae and sexually transmitted diseases.

Examples of viral infections include but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), Colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever.

Examples of bacterial infections include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, salmonellosis, scarlet fever, shigellosis, syphilis, tetanus, trachoma, tularemia, typhoid fever, and urinary tract infections.

Examples of parasitic infections include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include, but are not limited to, candidiasis, aspergillosis, coccidioidomycosis, cryptococcosis, histoplasmosis and tinea pedis Typically antagonist may be used in combination with radiotherapy and hormone therapy.

Typically said antagonist may also be used in combination with a one or more agents selected from the group consisting of an anticancer agent, an antiemetic agent, an hematopoietic colony stimulating factor, an analgesic agent and an anxiolytic agent.

In one embodiment, said antagonist is a selected in the group consisting of HVEM ligand. Preferably, said antagonist is a soluble HVEM ligand. The person skilled in the art may refer to the publication Pasero et al., "*The HVEM network: new directions in targeting novel costimulatory/co-inhibitory molecules for cancer therapy*", Current opinion in Pharmacology 2012; 12:478-485.

Typically, said ligand is selected in the group consisting of BTLA, LIGHT, LTα, glycoprotein D and CD160. Preferably, said soluble HVEM ligand is recombinant.

Preferably, said antagonist is selected from the group consisting of a soluble recombinant BTLA, a soluble recombinant LIGHT, a soluble recombinant LIGHT, a soluble recombinant CD160 or a fragment thereof which blocks the interaction between BTLA and HVEM. More preferably, said antagonist is a recombinant BTLA.

In another embodiment, said antagonist is chosen from antibodies directed against HVEM and fragments thereof which block the interaction between BTLA and HVEM.

Typically, said antagonist is an antibody. Preferably, said antibody is chosen among polyclonal antibody, monoclonal antibody, chimeric antibody, humanized antibody, or an antibody fragments.

Preferably, said antibody is a monoclonal antibody.

The term "antibody" is further intended to encompass antibodies, digestion fragments, specified portions and variants thereof, including antibody mimetics or portions of antibodies that mimic the structure and/or function of an antibody or specified fragment or portion thereof, including single chain antibodies and fragments thereof. Functional fragments include antigen-binding fragments that block the interaction between HVEM and BTLA.

As used herein, the term "human antibody" refers to an antibody in which a substantial portion of the antibody molecule resembles, in amino acid sequence or structure, that of an antibody derived from human origin. The term "humanized antibody" refers to an antibody which has been modified by genetic engineering or by other means to be similar in structure or amino acid sequence to naturally occurring human antibodies. A "human antibody" or a "humanized antibody" may be considered more suitable in instances where it is desirable to reduce the immunogenicity of the antibody for administration to humans for therapeutic, prophylactic or diagnostic purposes.

Antibodies specifically directed against HVEM may be derived from a number of species including, but not limited to, rodent (mouse, rat, rabbit, guinea pig, hamster, and the like), porcine, bovine, equine or primate and the like. Antibodies from primate (monkey, baboon, chimpanzee, etc.) origin have the highest degree of similarity to human sequences and are therefore expected to be less immunogenic. Antibodies derived from various species can be "humanized" by modifying the amino acid sequences of the antibodies while retaining their ability to bind the desired antigen. Antibodies may also be derived from transgenic animals, including mice, which have been genetically modified with the human immunoglobulin locus to express human antibodies. Procedures for raising "polyclonal antibodies" are well known in the art. For example, polyclonal antibodies can be obtained from serum of an animal immunized against HVEM, which may be produced by genetic engineering for example according to standard methods well-known by one skilled in the art. Typically, such antibodies can be raised by administering HVEM protein subcutaneously to New Zealand white rabbits which have first been bled to obtain pre-immune serum. The antigens can be injected at a total volume of 100 μl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times at six weeks' interval. A sample of serum is then collected 10 days after each boost. Polyclonal antibodies are then recovered from the serum by affinity chromatography using the corresponding antigen to capture the antibody. This and other procedures for raising polyclonal antibodies are disclosed by (Harlow et al., 1988), which is hereby incorporated in the references.

Although historically monoclonal antibodies were produced by immortalization of a clonally pure immunoglobulin secreting cell line, a monoclonally pure population of antibody molecules can also be prepared by the methods of the present invention.

Laboratory methods for preparing monoclonal antibodies are well known in the art (see, for example, Harlow et al., 1988).

A "monoclonal antibody" or "mAb" in its various names refers to a population of antibody molecules that contains only one species of antibody combining site capable of immunoreacting with a particular epitope. A monoclonal antibody thus typically displays a single binding affinity for any epitope with which it immunoreacts. Monoclonal antibody may also define an antibody molecule which has a plurality of antibody combining sites, each immunospecific for a different epitope. For example, a bispecific antibody would have two antigen binding sites, each recognizing a different interacting molecule, or a different epitope. As used herein, the terms "antibody fragment", "antibody portion", "antibody variant" and the like include any protein or polypeptide containing molecule that comprises at least a portion of an immunoglobulin molecule such as to permit specific interaction between said molecule and an antigen (e.g. HVEM). The portion of an immunoglobulin molecule may include, but is not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of a ligand or counter-receptor (e.g. LIGHT, BTLA or HSV-gD) which can be incorporated into an antibody of the present invention to permit interaction with the antigen (e.g. HVEM).

Monoclonal antibodies (mAbs) may be prepared by immunizing a mammal such as mouse, rat, primate and the like, with purified HVEM protein. The antibody-producing cells from the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in (Kohler and Milstein, 1975). Alternatively, the immunoglobulin genes may be isolated and used to prepare a library for screening for reactive specifically reactive antibodies. Many such techniques including recombinant phage and other expression libraries are known to one skilled in the art.

While mAbs can be produced by hybridoma culture the invention is not to be so limited. Also contemplated is the use of mAbs produced by cloning and transferring the nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

In a particular embodiment, mAbs recognizing HVEM may be generated by immunization of Balb-c mice with the respective recombinant human Fc-IgG1 fusion proteins. Spleen cells were fused with X-63 myeloma cells and cloned according to already described procedures (Olive D, 1986). Hybridoma supernatants were then screened by staining of transfected cells and for lack of reactivity with untransfected cells.

Antibody generation techniques not involving immunisation are also contemplated such as for example using phage display technology to examine naive libraries (from non-immunised animals); see (Barbas et al., 1992, and Waterhouse et al. (1993). Antibodies of the invention are suitably separated from the culture medium by conventional immunoglobulin purification procedures such as, for example, affinity, ion exchange and/or size exclusion chromatography, and the like.

In a particular embodiment, the antibody of the invention may be a human chimeric antibody. Said human chimeric antibody of the present invention can be produced by obtaining nucleic sequences encoding VL and VH domains, constructing a human chimeric antibody expression vector by inserting them into an expression vector for animal cell having genes encoding human antibody CH and human antibody CL, and expressing the expression vector by introducing it into an animal cell. The CH domain of a human chimeric antibody may be any region which belongs to human immunoglobulin, but those of IgG class are suitable and any one of subclasses belonging to IgG class, such as IgG1, IgG2, IgG3 and IgG4, can also be used. Also, the CL of a human chimeric antibody may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

In another particular embodiment, said antibody may be a humanized antibody. Said humanized antibody may be produced by obtaining nucleic acid sequences encoding for CDRs domain by inserting them into an expression vector for animal cell having genes encoding a heavy chain constant region identical to that of a human antibody; and a light chain constant region identical to that of a human antibody, and expressing the expression vector by introducing it into an animal cell.

The humanized antibody expression vector may be either of a type in which a gene encoding an antibody heavy chain and a gene encoding an antibody light chain exist on separate vectors or of a type in which both genes exist on the same vector (tandem type). In respect of easiness of construction of a humanized antibody expression vector, easiness of introduction into animal cells, and balance between the expression levels of antibody H and L chains in animal cells, a tandem type of the humanized antibody expression vector is more preferable (Shitara K et al. 1994). Examples of the tandem type humanized antibody expression vector include pKANTEX93 (WO 97/10354), pEE18 and the like. Methods for producing humanized antibodies based on conventional recombinant DNA and gene transfection techniques are well known in the art (See, e.g. Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Preferably, said fragment of the antibody which blocks the interaction between BTLA and HVEM interaction is chosen among Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments.

Such fragments may be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

Said Fab fragment of the present invention can be obtained by treating an antibody which specifically reacts with human HVEM with a protease, papaine. Also, the Fab may be produced by inserting DNA encoding Fab of the antibody into a vector for prokaryotic expression system or for eukaryotic expression system, and introducing the vector into a prokaryote or eucaryote to express the Fab.

Said F(ab')$_2$ of the present invention may be obtained by treating an antibody which specifically reacts with HVEM with a protease, pepsin. Also, the F(ab')$_2$ can be produced by binding Fab' described below via a thioether bond or a disulfide bond.

Said Fab' may be obtained by treating F(ab')$_2$ which specifically reacts with HVEM with a reducing agent, dithiothreitol. Also, the Fab' can be produced by inserting DNA encoding Fab' fragment of the antibody into an expression vector for prokaryote or an expression vector for eukaryote, and introducing the vector into a prokaryote or eukaryote to effect its expression.

Said scFv fragment may be produced by obtaining cDNA encoding the V$_H$ and V$_L$ domains as previously described, constructing DNA encoding scFv, inserting the DNA into an expression vector for prokaryote or an expression vector for eukaryote, and then introducing the expression vector into a prokaryote or eukaryote to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. No. 5,859,205; U.S. Pat. No. 5,585,089; U.S. Pat. No. 4,816,567; EP0173494).

In a particular embodiment, monoclonal antibodies of the invention are monovalent, bivalent, multivalent, monospecific, bispecific, or multispecific. In another preferred embodiment, the antibody directed against HVEM is a binding fragment or a conjugate. For examples antibodies of the invention may be conjugated to a growth inhibitory agent, cytotoxic agent, or a prodrug-activating enzyme.

It may be also desirable to modify the antibody of the invention with respect to effector functions, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992) Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non-proteinaceous polymers, e.g. polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

In a preferred embodiment said anti-HVEM antibody is a monoclonal antibody obtainable from the hybridoma deposited at the Collection Nationale de Cultures de Microorganismes (CNCM, Institut Pasteur, 25 rue du Docteur Roux, 75724 Paris Cedex 15, France), in accordance with the terms of Budapest Treaty, on May 16, 2013, under the number CNCM I-4752.

As used herein, the expression "HVEM 18.10" refers to an isolated HVEM antibody which is obtainable from the hybridoma accessible under CNCM deposit number I-4752.

In still another embodiment, said antagonist is chosen from antibodies directed against BTLA and fragments thereof which block the interaction between BTLA and HVEM.

Preferably, said antibodies increase the proliferation of Vγ9Vδ2 T cells. Therefore, they are highly efficient in a method for treating hematologic malignancies, solid tumors, autoimmune diseases and infections.

The previously disclosed technical features apply to said antibodies directed against BTLA.

Preferably, said antagonist is an antibody obtainable from a hybridoma deposited at the Collection Nationale de Cultures de Microorganismes (CNCM, Institut Pasteur, 25 rue du Docteur Roux, 75724 Paris Cedex 15, France), in accordance with the terms of Budapest Treaty, on Feb. 4, 2009, under the number CNCM I-4123.

As used herein, the expression "BTLA8.2" refers to an isolated BTLA antibody which is obtainable from the hybridoma accessible under CNCM deposit number I-4123.

A further object of the invention relates to a hybridoma cell line suitable for obtaining monoclonal antibodies directed against HVEM, which increases the proliferation of Vγ9Vδ2 T cells.

Preferably, said hybridoma cell line is the hybridoma cell line deposited at the Collection Nationale de Cultures de Microorganismes on May 16, 2013, under the number CNCM I-4752.

The term "hybridoma" denotes a cell, which is obtained by subjecting a B cell, prepared by immunizing a non-human mammal with an antigen, to cell fusion with a myeloma cell derived from a mouse or the like which produces a desired monoclonal antibody having an antigen specificity.

A further object of the invention relates to monoclonal antibody directed against HVEM which blocks the interaction between HVEM and BTLA and increases the proliferation of Vγ9Vδ2 T cells. Preferably, said monoclonal antibody is obtainable from the hybridoma deposited at the Collection Nationale de Cultures de Microorganismes on May 16, 2013, under the number CNCM I-4752.

A further object of the invention relates to a method of treating hematologic malignancies, solid tumors, autoimmune diseases and infection comprising administering in a subject in need thereof a therapeutically effective amount of an antagonist as defined above.

In the context of the invention, the term "treating" or "treatment", as used herein, means reversing, alleviating, inhibiting the progress of, or preventing the disorder or condition to which such term applies, or one or more symptoms of such a disorder or condition.

As used herein, the term "subject" denotes a mammal, such as a rodent, a feline, a canine, and a primate. Preferably a subject according to the invention is a human.

According to the invention, the term "patient" or "patient in need thereof" is intended for a human or non-human mammal affected or likely to be affected by a hematologic malignancies, a solid tumor an autoimmune disease or infection.

By a "therapeutically effective amount" of the antagonist of the BTLA/HVEM according to the invention is meant a sufficient amount of the antagonist of the BTLA/HVEM to treat said hematologic malignancy, solid tumor, autoimmune disease, or infection at a reasonable benefit/risk ratio applicable to any medical treatment. It will be understood, however, that the total daily usage of the ligand of HVEM and compositions of the present invention will be decided by the attending physician within the scope of sound medical judgment. The specific therapeutically effective dose level for any particular patient will depend upon a variety of factors including the disorder being treated and the severity of the disorder, activity of the specific antagonist of the BTLA/HVEM employed; the specific composition employed, the age, body weight, general health, sex and diet of the patient, the time of administration, route of administration, and rate of excretion of the specific antibody employed, the duration of the treatment; drugs used in combination or coincidental with the specific polypeptide employed, and like factors well known in the medical arts. For example, it is well known within the skill of the art to start doses of the compound at levels lower than those required to achieve the desired therapeutic effect and to gradually increase the dosage until the desired effect is achieved.

Antagonists of the BTLA/HVEM to the invention may be used in combination with any other therapeutic strategy for treating the disorders or conditions as above described (e.g. external radiotherapy, chemotherapy or cytokine therapy).

A further object of the invention relates to a pharmaceutical composition comprising an effective dose of an antagonist of the BTLA/HVEM.

Any therapeutic agent of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of antagonist of the BTLA/HVEM may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

Antagonist of the BTLA/HVEM interaction of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

Compositions of the present invention may comprise a further therapeutic active agent. The present invention also relates to a kit comprising a ligand of HVEM as defined above and a further therapeutic active agent.

In one embodiment said therapeutic active agent is an anticancer agent. For example, said anticancer agents include but are not limited to fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A. In one embodiment, additional anticancer agents may be selected from, but are not limited to, one or a combination of the following class of agents: alkylating agents, plant alkaloids, DNA topoisomerase inhibitors, antifolates, pyrimidine analogs, purine analogs, DNA antimetabolites, taxanes, podophyllotoxin, hormonal therapies, retinoids, photosensitizers or photodynamic therapies, angiogenesis inhibitors, antimitotic agents, isoprenylation inhibitors, cell cycle inhibitors, actinomycins, bleomycin, anthracyclines, MDR inhibitors and Ca2+ATPase inhibitors.

Additional anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or muti-specific antibodies, monobodies, polybodies.

Additional anticancer agent may be selected from, but are not limited to, growth or hematopoietic factors such as erythropoietin and thrombopoietin, and growth factor mimetics thereof.

In the present methods for treating cancer the further therapeutic active agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoemanolamine, alizapride, azasetron, benzquinamide, bietanautine, bromopride, buclizine, clebopride, cyclizine, dunenhydrinate, diphenidol, dolasetron, meclizme, methallatal, metopimazine, nabilone, oxypemdyl, pipamazine, scopolamine, sulpiride, tetrahydrocannabinols, thiefhylperazine, thioproperazine and tropisetron. In a preferred embodiment, the antiemetic agent is granisetron or ondansetron.

In another embodiment, the further therapeutic active agent can be an hematopoietic colony stimulating factor. Suitable hematopoietic colony stimulating factors include, but are not limited to, filgrastim, sargramostim, molgramostim and epoietin alpha.

In still another embodiment, the other therapeutic active agent can be an opioid or non-opioid analgesic agent.

Suitable opioid analgesic agents include, but are not limited to, morphine, heroin, hydromorphone, hydrocodone, oxymorphone, oxycodone, metopon, apomorphine, nomioiphine, etoipbine, buprenorphine, mepeddine, lopermide, anileddine, ethoheptazine, piminidine, betaprodine, diphenoxylate, fentanil, sufentanil, alfentanil, remifentanil, levorphanol, dextromethorphan, phenazodne, pemazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In yet another embodiment, the further therapeutic active agent can be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

The invention will be further illustrated through the following examples, figures and tables.

FIGURES

BTLA blockade (with full length BTLA 8.2 or its Fab form) increases the phosphorylation of Zap-70 and Erk1/2. $1 \times 10^6$ purified γδ T cells derived from a HV were stimulated for 5 minutes with BrHPP (50 nM) and isotype control or anti-PD-1.3.1 mAb or anti BTLA 8.2. Total cellular proteins were separated on 10% SDS-PAGE 544 and revealed by western blot analysis using the phospho-Zap-70 or phospho-Erk1/2 antibody.

Circulating γδ cells from HV were purified and cultured with IL-2+/−25 to 1000 nM BrHPP during 5 days (n=3). Proliferation was quantified by CFSE dilution and represented as the percentage of divided cells among the γδ T cells.

CellTrace dilution in purified-γδ T cells from 4 HV stimulated 5 days with or without low dose BrHPP (50 nM) with specified mAb or FC-proteins. Results were expressed as mean+/−SEM and statistical significance was established using the non-parametric paired Wilcoxon U-test.

*$p<0.05$; $0.001<p<0.01$; *$p<0.001$.

Percentage of naive Vγ9Vδ2 T cells in S phase (upper panel) or in G2/M phase (lower panel) after 3 days in culture with IL2+BrHPP+/−IgG1 or HVEM 11.8 (n=12). Cells that may be in transition between two proliferation stages were excluded. Results were expressed as mean+/−SEM and statistical significance was established using the non-parametric paired Wilcoxon U test. *$p<0.05$; $0.001<p<0.01$; *$p<0.001$.

Percentage of BTLA positive cells among Vγ9Vδ2 T cells from patients with inflammatory lymph nodes (IF-LN), non-Hodgkin lymphoma (NHL), and Hodgkin lymphoma (HL).

CellTrace dilution gated on intra-nodal γδ T cells (n=11) stimulated 5 days with IL-2 and specified mAb. Results were expressed as mean+/−SEM and statistical significance was established using the non-parametric paired Wilcoxon U-test.

*$p<0.05$; $0.001<p<0.01$; *$p<0.001$.

EXAMPLES

Material & Methods

Patients

Eleven lymph nodes from lymphoma patients were evaluated including 9 NHLs and 3 Hodgkin lymphoma (HL), NHLs samples were classified as B-cell follicular lymphoma (FL, n=7) and diffuse large B-cell lymphoma (DLBCL, n=1). HLs samples belonged to the classical form. Informed consent was obtained from all participants in accordance with the Declaration of Helsinki. The study was approved by the institutional review boards of the Institut Paoli Calmettes. The control group consisted of seven healthy volunteers (HV) provided by Marseille Blood Bank. Mononuclear cells from lymph nodes were isolated after mechanical disruption. Peripheral blood mononuclear cells from HV were isolated by density gradient centrifugation (Lymphoprep, Abcys). Isolated cells were viably frozen in fetal bovine serum (PAN Biotech) containing 10% dimethyl sulfoxide (Sigma-Aldrich) until use.

Reagents and Antibodies

Bromohydrin pyrophosphate (BrHPP) was obtained from Innate Pharma (Marseille, France) with recombinant human IL2 (rIL2) purchased from BD Biosciences (San Jose, Calif., USA). The mAbs and FC protein used for functional experiments and immunofluorescence analysis are listed in table I in supplementary data.

Generation of Anti-Human HVEM, BTLA and PD-1 Monoclonal Antibodies (mAbs)

mAbs recognizing BTLA (clones 8.2); HVEM (HVEM 11.8, HVEM 18.10) and PD-1 (PD1.3.1) were generated as previously described. Fab fragments were generated using the Fab preparation kit (Thermo Scientific Pierce) according to the supplier's protocol.

Characterization of New HVEM-Specific mAbs (HVEM-11.8 and 18.10)

Stable LTK-HVEM ($2 \times 10^5$ cells) transfectants were treated with a mixture of 10 μg/ml of BTLA-Fc and a range of concentrations (0.001-30 μg/ml) of HVEM-11.8 or 18.10 mAb for 1 hour at 4° C. Cells were then washed with PBS and stained with R-PE-conjugated AffiniPure F(ab')2 131 Fragment Goat Anti-Human IgG (H+L) (Immunotech) for 30 min at 4° C. To measure the inhibition activity, the PD1-3 mAb was included in the same conditions as non-blocking control. Binding of HVEM-Fc and blocking activity of either HVEM-11.8 or 18.10 mAb were determined by flow cytometry on a BD FACScan cytometer. For HVEM-Fc protein, extracellular domain (Met1-Val202) of HVEM fused to the Fc protein of human I 135 gG1 was cloned into the expression vector Cos Fc Link (SmithKline Beecham Pharmaceuticals). For HVEM ΔCRD1-Fc protein, extracellular domain deleted from its CRD1 domain fused to the Fc protein of human IgG1 was cloned into the expression vector Cos Fc Link (SmithKline Beecham Pharmaceuticals). For HVEM V74A-Fc protein, Val74 was mutated into Alanine.

Cell Culture

Effector-γδ T cells were established and maintained as previously described. 15 Briefly, PBMC were stimulated by BrHPP (3 μM) and rIL2 (100 IU/ml). rIL-2 was renewed every two days and cells were maintained at 1.5×106 cells/ml. The FL cell lines RL and Karpas-422 were cultured (0.5.106/ml) in complete RPMI 1640 medium supplemented with 10% heat-inactivated FCS.

Flow Cytometry

2·10$^5$ PBMCs were washed in PBS (Cambrex Bio Science) and incubated at 4° C. for 20 min with the specified mAb conjugates. Following incubation and washing, samples were analyzed on a LSRFortessa (Becton Dickinson) using the DIVA software (BD bioscience, Mountain View, Calif.).

Proliferation Assay

Purified γδ were labeled with 2.504 CFSE (Molecular Probes, LifeTech) for 10 minutes at 37° C. or with CellTrace Violet (Molecular Probes, LifeTech) for 10 minutes at 37° C. 2.105 CellTrace or CFSE-labeled cells were cultured in 96-well plates with or without indicated mAb or increasing doses of BrHPP. After 5 days of culture in the presence of 200 U/mL IL-2, CellTrace or CFSE dilution was evaluated by flow cytometry.

Cell Cycle Analysis

After 3 and 4 days in culture with IL-2+BrHPP, purified γδ T cells were cultured with 1504 BrdU for 1 hour then fixed, permeabilized and stained for BrdU and 7-AAD according to the manufacturer instruction (FITC BrdU Flow Kit, BD Pharmingen). Flow cytometry analysis of cell incorporated BrdU (with FITC anti-BrdU) and total DNA content (with 7-AAD) in purified γδT cells allowed for the discrimination of cell subset that were apoptotic (7-AAD-neg), or in G0/G1 (BrDU+, 4-AADlow), S (BrDU+) or G2/M (BrDUneg, 7AADbright) phases of the cell cycle.

Immunofluorescence

After 30 minutes of sedimentation on poly-L-lysine pretreated coverslip, purified γδ from HV were fixed in methanol at −20° C. for 6 minutes and washed in PBS. After blocking in PBS 10% SVF, cells were incubated with primary antibodies: TCRVδ2 mAb and BTLA mAb for 1 hour. After washing in PBS, 0.1% Tween20, BTLA staining was detected using anti-IgG secondary antibodies conjugated to Cyanine 5 (Cy5) from Jackson Laboratories. Sequential staining was used in order to prevent artificial co-localization due to secondary antibody. DNA was stained with 250 ng/ml DAPI (Roche diagnostics) during secondary staining Cells were mounted in Prolong Gold anti-fade reagent (Invitrogen) and examined on a LSM-510 Carl Zeiss confocal microscope with a X63 NA1.4 Plan Apochromat objective.

Western Blot 1.106 γδ T cells were treated for 5 minutes with low dose BrHPP in RPMI medium with 10% serum. Cells were then placed on ice, washed in PBS, and lysed in 20 μl of ice-cold HNTG buffer (50 mM HEPES pH 7, 50 mM NaF, 1 mM EGTA, 150 mM NaCl, 1% Triton X-100, 10% glycerol, and 1.5 mM MgCl2) in the presence of protease inhibitors (Roche Applied Science) and 100 μM Na3VO4. Proteins were resolved by SDS-PAGE 10%, followed by western blotting. Primary antibodies used were from cell signaling: rabbit anti-phospho-Zap70 antibody and rabbit anti-phospho-Erk1/2 antibody. Primary antibodies were detected with horseradish peroxidise conjugated anti-rabbit antibody (Jackson Laboratory). Immunoreactive bands were detected sing enhanced chemiluminescent reagents (Pierce).

Statistics

Results are expressed as median±SEM. Statistical analysis was performed using Wilcoxon test and Mann-Whitney t test. P values<0.05 were considered significant. The GraphPad Prism statistical analysis program was used.

Results

BTLA Expression is Inversely Correlated with Vγ9Vδ2 T Cell Differentiation

The inventors determined the expression of BTLA in Vγ9Vδ2 T cells by performing ex vivo multicolor flow cytometry analysis on PBMCs from HV. BTLA was strongly expressed at the surface of resting Vγ9Vδ2 T cells (52.5%±5), unlike PD-1 which was expressed at minimal level as previously shown and other co-signaling molecules such as CTLA-4 and ICOS which were absent. They next verified whether BTLA expression varied pending on the developmental status of Vγ9Vδ2 T cells defined by CD45RA and CD27 expression BTLA was primarily expressed on naive (N; CD45RA+CD27+) and central-memory T cells (CM; CD45RA-CD27+), and to a lesser extent on effector memory T cells (EM, CD45RA2 CD27−). Hence, in line with data obtained on CD8+αβ T cells, where BTLA is found on naive T cells and is progressively downregulated in memory and differentiated effector-type cells, BTLA expression inversely correlated with Vγ9Vδ2 T cell differentiation. As a control, the inventors studied the expression of PD-1 in the various γδ T cell subsets which was present on all subsets with preferential expression on effector memory population (TemH1; CD45RA-CD27−).

BTLA and TCR are Concurrently Down-Regulated During Activation

The inventors next determined whether BTLA expression was regulated during Vγ9Vδ2 T-cell activation. Vγ9Vδ2 T cells were stimulated with IL-2 alone or in combination with the synthetic PAg BrHPP and monitored over a period of 5 days. The intensity of BTLA expression was constant in IL-2 treated cells, whereas expression significantly decreased after 24 h following IL-2+BrHPP stimulation (p=0.002; and returned to baseline at 72 hours.) The inventors found a concurrent down-regulation of BTLA and TCR induced by BrHPP, but not with IL-alone, consistently with previous studies on αβT cells, PD-1 expression was significantly up-regulated at 24 hrs under BrHPP stimulation.

Figure 1:
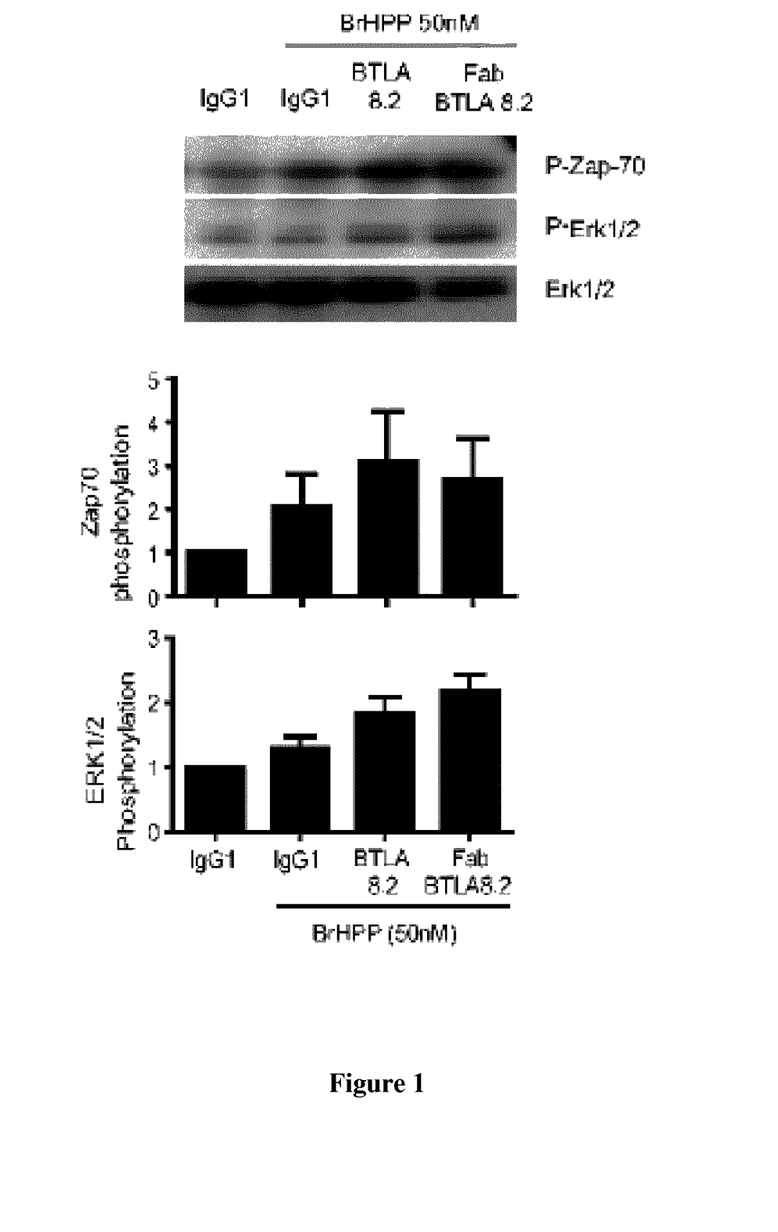
FIG. 1: BTLA co-localized with Vγ9Vδ2TCR after activation

Upon Activation, BTLA is Clustered Close to the TCR and Reduces TCR-Mediated Signaling The observation of correlated regulation of TCR and BTLA expression at the surface of Vγ9Vδ2 T cells indicates a potential physical relationship. Consequently, the inventors next investigated the subcellular localization of BTLA upon TCR-mediated activation. The inventors first activated Vγ9Vδ2 T cells with PAg and followed the TCR and BTLA localization by confocal microscopy. As expected, BTLA was localized close to the TCR. This applies even after polarization induced by a HVEM+ lymphoma cell line. They observed a clustering of BTLA and the TCR at the synapse between Vγ9Vδ2T cells and target cells. Of note, the two Vγ9Vδ2 T cells shown on DIC image appear differently with respect to BTLA expression, which can be explained by the fact that the inventors used a bulk population of Vγ9Vδ2 T cells that includes all differentiation stages with different level of BTLA expression. The close localization of the TCR and BTLA suggested that BTLA engagement could affect TCR dependent signaling. Vγ9Vδ2 T cells were then stimulated via the TCR, using PAg stimulation, in the presence or absence of an anti-BTLA blocking antibody. As observed in FIG. 1, phosphorylation of ZAP-70 and Erk1/2 was increased after BTLA blockade.

These data indicate that BTLA negatively regulates TCR-mediated activation.

Figure 2:
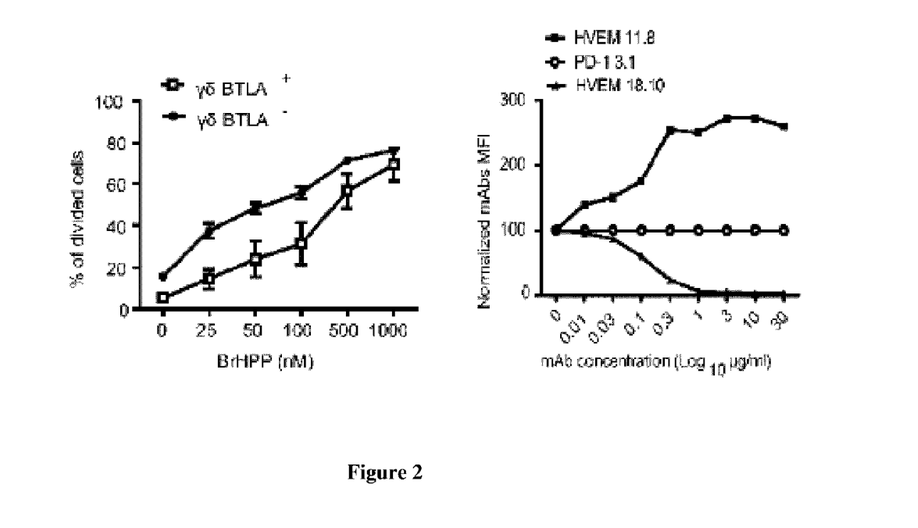
FIG. 2: BTLA-HVEM interaction inhibited γδ T cell proliferation.
Figure 3:
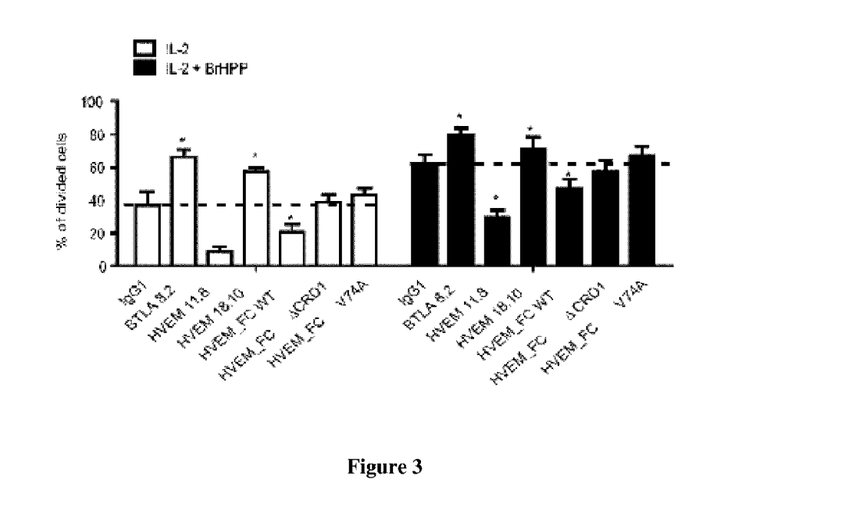
FIG. 3: BTLA-HVEM interaction inhibited γδ T cell proliferation.

BTLA Engagement by its Ligand HVEM Attenuates Vγ9Vδ2 T Cell Proliferative Capacities TCR-mediated activation of Vγ9Vδ2 T cells usually results in cytotoxicity and cytokine production. Surprisingly, BTLA blockade affected neither degranulation nor production of pro inflammatory cytokines (IFN-γTNFα of PAg-stimulated Vγ9Vδ2 T cells. After activation and triggering of effector functions, Vγ9Vδ2 T cells undergo rapid proliferation. They next studied whether BTLA could affect this proliferation. Highly purified Vγ9Vδ2 T cells were stimulated by IL-2+BrHPP and their proliferation capacities was assessed by CFSE dilution together with the monitoring of BTLA expression. Interestingly, the subset of Vγ9Vδ2 T cells with the highest proliferative potential was the BTLA negative population named "γδBTLA-" on FIG. 2. The inventors next studied the role of BTLA-HVEM interaction with respect to proliferation, using mAb directed against BTLA, or its ligand HVEM, generated by the inventors. The HVEM 11.8 mAb efficiently increased the binding of BTLA to HVEM expressing cells whereas the HVEM 18.10 mAb was selected for its ability to efficiently block this interaction (FIG. 3), and therefore has the same effect as the previously described antagonistic BTLA 8.2. Since the HVEM binding site for BTLA involves almost exclusively residues from CRD1, the inventors generated two HVEM-FC mutants: HVEM-ACRD1 (deleted for the CRD1 domain), which had lost its ability to interact with BTLA, and HVEM-V74A (mutation of HVEM residue Val36 to alanine), which resulted in a 10-fold reduction in BTLA affinity. When BTLA was engaged by its ligand HVEM (HVEM-Fc), the inventors observed a significant inhibition of Vγ9Vδ2 T cell proliferation induced by IL-2+BrHPP 261 (FIG. 3). Conversely, the blockade of BTLA-HVEM interaction with antagonist mAbs (BTLA 8.2 and HVEM 18.10) resulted in a significant increase in proliferation induced by IL-2+BrHPP (FIG. 3 right histogram). Importantly, the blocking effects of BTLA 8.2 or HVEM 18.10 mAbs were also observed without TCR stimulation by BrHPP (IL-2 alone, FIG. 3 left histogram), which stress out that the negative role of BTLA may be independent from the TCR signaling pathway. As a control, the two mutants of HVEM-Fc have no effect on Vγ9Vδ2 T cell proliferation. These data showed that BTLA-HVEM interaction is a major pathway implicated in the negative regulation of Vγ9Vδ2 T cell proliferation. Since BTLA expression was modulated during Vγ9Vδ2 T cell differentiation, the inventors hypothesized that the inhibition of proliferation by BTLA may differ between the different differentiation stages of Vγ9Vδ2 T cells. Total Vγ9Vδ2 T cells were sorted by flow cytometry on the basis of CD45RA and CD27 expression and put in culture with IL-2+BrHPP for 5 days. BTLA-HVEM interaction similarly affected both proliferation and activation of naïve cells and cells which have already encountered Ag. Interestingly, a better binding of HVEM to BTLA limited the naive and CM cells transition to effector cells.

Altogether these data support a role of BTLA as a regulator Vγ9Vδ2 T cell proliferation, activation and differentiation.

BTLA-HVEM Interaction Induces Partial S Phase Arrest

Figure 4:
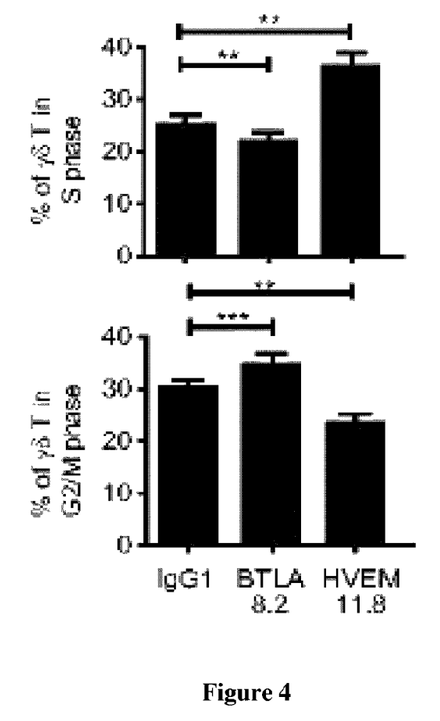
FIG. 4: BTLA-HVEM engagement induce partial S phase arrest

The results indicated that, like the B7-CTLA-4 pathway 43,44 BTLA-HVEM interaction might exert its major effect on Vγ9Vδ2 T cell immune response via regulation of the cell cycle. Treatment with agonistic anti-HVEM mAb of IL-2+BrHPP stimulated Vγ9Vδ2 T cells, resulted in a significantly higher percentage of phenotypically naive cells in S phase ($p=0.0024$; FIG. 4) as compared to anti-IgG1-treated Vγ9Vδ2 T cells. The percentage of subG0 cells (apoptotic cells) was not affected by engagement of BTLA, suggesting that after exposure to mAb for 72 hours, Vγ9Vδ2 T cells do not undergo apoptosis. Conversely, blocking BTLA engagement resulted in a slight but significant ($p=0.0049$) decrease in the percentage of cells in S phase and increase ($p=0.0005$) in G2/M phase (FIG. 4). Altogether, these data showed that BTLA engagement reduces Vγ9Vδ2 T cell proliferation capabilities as a result of partial S phase arrest.

Figure 5:
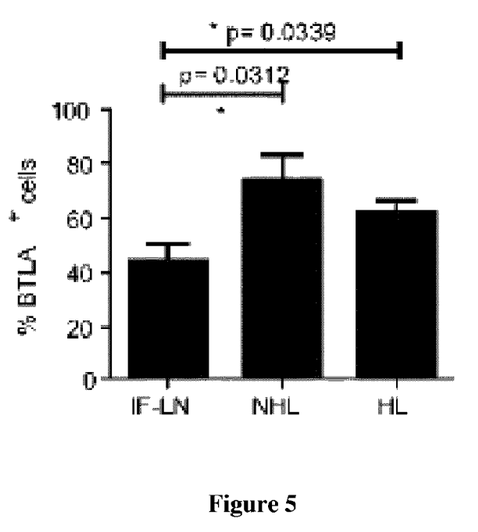
FIG. 5: BTLA blockade restored γδ T cell proliferation in co-culture with HVEM+ lymphoma cells.
Figure 6:
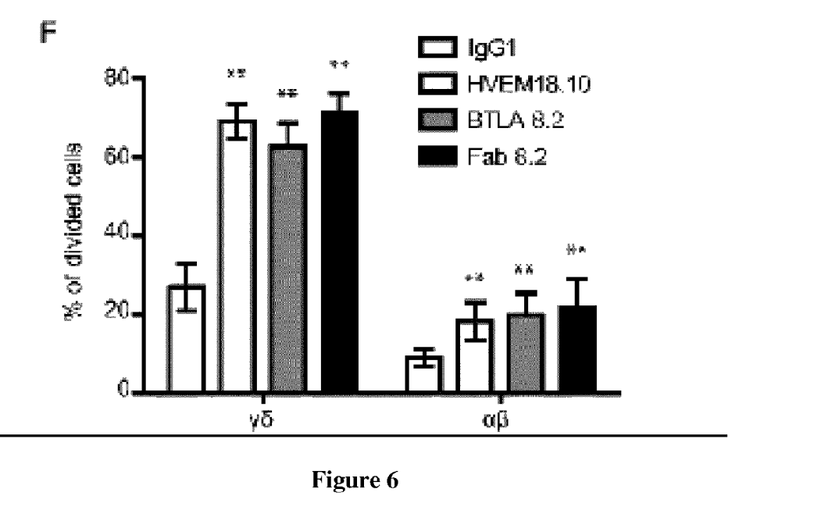
FIG. 6: BTLA blockade restored γδ T cell proliferation in co-culture with HVEM+ lymphoma cells.

BTLA-HVEM Blockade Increases Vγ9Vδ2 T Cell Proliferation in Co-Culture with HVEM+Lymphoma Cells Insofar as HVEM is widely expressed by other immune cells, notably by B cells, but also by tumor cells, the inventors next wondered whether HVEM-expressing tumor cells could affect Vγ9Vδ2 T cell proliferation. First of all, the inventors used two FL cell lines RL and Karpas-422. These two cell lines expressed HVEM but not CD160 and LIGHT. CellTrace labelled Vγ9Vδ2 T cells were then co-incubated for 5 days with or without irradiated FL cell lines in the absence or presence of IL-2+BrHPP. The inventors first observed that lymphoma cell lines induced a significant decrease of CellTrace dilution in BrHPP-treated Vγ9Vδ2 T cells compared to BrHPP treated Vγ9Vδ2 T cells alone ($p=0.0117$, Blockade of BTLA with antagonist mAbs strongly increased the proliferation of Vγ9Vδ2T cells. Although B cells express high amounts of Fc receptor, the Fab of anti-BTLA 8.2 resulted in a similar increase of proliferation. To investigate BTLA-HVEM interactions in the tumor microenvironment the inventors have mechanically disrupted lymph nodes from eleven patients with several types of lymphoma and re-suspended cells to perform multi-parametric flow cytometry analysis. On each sample the inventors evaluated the HVEM expression on neoplastic cells ($69.3\% \pm 6.88$ on NHL) (FIG. 5) and the expression of BTLA, CD160 and LIGHT on cytotoxic effectors present in tumor microenvironment such as NK cells, αβT cells and γδ T cells (FIG. 5). The inventors found that BTLA is restricted to the T cell compartment ($59\% \pm 5.3$ and $57.7\% \pm 7.4$ on αβT cells and γδ T cells respectively) whereas CD160 and LIGHT were absent. Vγ9Vδ2 T cells were mostly of the CM phenotype and their BTLA expression profile was in line with that of HV. Hence, BTLA appears as the main ligand for HVEM present on the tumor microenvironment. The inventors next stained Vγ9Vδ2 T cells with CellTrace to assess their proliferative capacities after five days of coculture with autologous lymphoma cells and IL-2 in the presence or absence of blocking mAb directed against HVEM or BTLA. The blockade of BTLA-HVEM interaction resulted in a significant increase (HVEM 18.10 $p=0.0029$; BTLA 8.2 $p=0.0049$ or Fab BTLA 8.2 $p=0.0078$) in Vγ9Vδ2 T cells proliferation. Notably the inventors found similar results with αβT cells (FIG. 6).

Altogether these data showed that HVEM positive lymphoma cells have the potential to reduce the proliferation of intra-nodal Vγ9Vδ2 T cells in BTLA-dependent manner.

CONCLUSION

The co-receptor BTLA has been extensively studied on conventional αβ T cells where it attenuates T cell activation and proliferation. The inventors have shown for the first time that BTLA is implicated in the regulation of Vγ9Vδ2 T cells proliferation and differentiation. In addition, BTLA-HVEM pathway is a major actor in the control of Vγ9Vδ2 T cells proliferation against lymphoma B cells. These findings have potent implications for the understanding of γδ T cells responses during the course of various diseases, viral infections, and cancer progression. The manipulation of these pathways is crucial for developing effective tumor immunotherapy.

The inventors first examined the expression of BTLA on different human peripheral blood γδ T cells subsets. The inventors observed that resting γδ T cells expressed high level of BTLA particularly on the naïve population. However this expression was down-regulated on CM and EM stages compared with γδ naïve T cells. In contrast, PD-1 is preferentially expressed on Temh1 γδ Tcells subsets. Moreover, PD-1 expression was up-regulated following TCR engagement whereas that of BTLA was drastically down-modulated. These data reveal a different regulation of expression of BTLA and PD-1, which may reflect different functions. For instance it has been suggested that PD-1 up-regulation may participate to the contraction of T cell immune response following an immune challenge. In contrast, BTLA may serve a regulator of immune response initiation, similarly to ICOS and B7 molecules. For instance, enhancing BTLA-HVEM interaction with agonistic mAbs resulted in a 25% reduction of the percentage of effector cells as compared to isotype control, after IL-2+BrHPP stimulation. This result indicates that this co signaling pathway may regulate human γδ T-cell differentiation. Accordingly, recent data showed a direct role of the B7/CTLA-4 interaction on the Th17 differentiation.

From a functional perspective, the present study provides evidence that BTLA is a new inhibitory molecule for human γδ T-cell activation. Hence, the inventors have shown that BTLA is expressed closely to the TCR at the surface of activated γδT cells, and at the synapse between γδ T cells and HVEM+ target cells. Western blot analyses showed that γδ TCR proximal signaling is improved after BTLA blockade, revealing BTLA as a repressor of γδ TCR signaling as previously described for γδTCR signaling. Critically these new observations may help the understanding of the kinetics of γδT-cells responses during the course of various autoimmune diseases and provide a basis for developing therapeutic approaches aimed at modulating over reacting inflammatory responses. At this point it is important to note that HVEM is also expressed by γδT cells. Hence, BTLA-HVEM interaction between γδT cells occurs in the absence of "target cells". Moreover, recent studies have revealed that HVEM and BTLA could interact in cis. Therefore, the use of a blocking anti-BTLA antibody as a single reagent is expected to induce a response in absence of a HVEM positive partner cell.

As a consequence of BTLA function on TCR signaling, the inventors have observed that BTLA negatively regulated γδ T cell proliferation, and that BTLA engagement during γδT cell activation induced a partial arrest in S phase. These data are consistent with previous data obtained on γδ T cells. Induction of γδ T cell response is associated, like for αβ T cells, with a strong expansion.

These data indicate that BTLA may participate to the regulation of this early event. Vγ9Vδ2 T cells are strongly activated and kill lymphoma cells. The anti-tumor activity of γδ T cells is largely dependent on cell-cell contact and their modulation by co-stimulatory and inhibitory signals may play a role in preventing γδ T-cell responses to tumors. In lymphoma tissue samples, the inventors observed that Vγ9Vδ2 T cells are present in low number and thus probably require extensive proliferation in order to conduct an efficient control of tumor progression. The inventors found that blockade of BTLA-HVEM interaction allowed a better spontaneous or TCR-induced proliferation of γδ T cell in co-culture with allogeneic and autologous HVEM+ lymphoma cells.

These data indicates that lymphoma cells may exert a control over γδT cell expansion using a BTLA-HVEM dependent pathway. Noteworthy, recent reports have described frequent loss-of function mutations in HVEM/TNFRSF14 in follicular lymphoma tissues. Launay et al. have identified several mutations in the TNFRSF14 gene that are correlated with a better prognosis. These data indicate that the loss of BTLA-HVEM interaction in the tumor microenvironment may favor γδ T cell expansion. However, further studies are required to confirm this putative model, since the prognostic value of TNFRSF14 mutation in lymphoma patients remains controversial. Larger series are also needed to perform statistical analyses comparing the proliferative capacities of intra-tumor γδT cells between HVEM-mutated and non-mutated lymphoma patients. Eventually, these data indicate a novel, previously un-described, pathway for tumor cell escape from γδT cell-mediated immune responses.

Hence, the invention provides an highly promising strategies for treating haematological malignancy, solid tumor, autoimmune disease or infection.

The invention claimed is:

1. An antagonist of the BTLA/HVEM interaction, wherein said antagonist is an antibody or a fragment thereof that increases the proliferation of Vγ9V62 T cells, wherein said antagonist is a monoclonal antibody directed against HVEM and produced by the hybridoma deposited at the Collection Nationale de Cultures de Microorganismes on May 16, 2013, under the number CNCM 1-4752.

2. The hybridoma cell line deposited at the Collection Nationale de Cultures de Microorganismes on May 16, 2013, under the number CNCM 1-4752.

3. A monoclonal antibody produced by the hybridoma deposited at the Collection Nationale de Cultures de Microorganismes on May 16, 2013, under the number CNCM 1-4752.

4. A monoclonal antibody having the complementarity determining regions of heavy and light chains of an antibody produced by the hybridoma deposited at the Collection Nationale de Cultures de Microorganismes on May 16, 2013, under the number CNCM I-4752.

* * * * *